United States Patent [19]
Gauldie et al.

[11] Patent Number: 4,973,478
[45] Date of Patent: Nov. 27, 1990

[54] TREATING INFLAMMATION WITH HEPATOCYTE STIMULATING FACTOR INTERFERON $\beta_2$

[75] Inventors: Jack Gauldie; Richards, Carl, both of Hamilton; Peter M. Lansdorp, Vancouver, all of Canada

[73] Assignee: Allelix Biopharmaceuticals, Inc., Ontario, Canada

[21] Appl. No.: 75,809

[22] Filed: Jul. 20, 1987

[51] Int. Cl.$^5$ .................... A61K 37/66; A61K 45/05; A61K 37/00; C12P 21/06
[52] U.S. Cl. .................. 424/85.4; 424/85.2; 435/69.51; 435/69.52; 514/12; 514/21; 514/893
[58] Field of Search ............. 424/85; 435/41, 68, 435/69.52, 85.21, 69.51; 514/12, 21, 893; 425/85.4, 85.2

[56] References Cited

U.S. PATENT DOCUMENTS 4,606,917  8/1986  Eppstein .................. 424/85

FOREIGN PATENT DOCUMENTS 89245   9/1983  European Pat. Off. .
107498  2/1984  European Pat. Off. .
119859  7/1984  European Pat. Off. .
215658  3/1987  European Pat. Off. .
217645  8/1987  European Pat. Off. .

OTHER PUBLICATIONS

Taniguchi, M. Chem. Abstr., vol. 106, Abstract No. 107907k, 1987.
Koj, A. et al., Biochem. J. vol. 224, pp. 505–514, (1984).
Gauldie et al., "Interferon $\beta_2$/B-cell . . . "Proc. Natl Acad. Sci., vol. 84, pp. 7251–7255, Oct. 1987.
Andus et al., "Recombinant Human B cell . . . "FEBS Letter, vol. 221, No. 1, pp. 18–22, Aug. 1987.
Patent Abstrcts of Japan, vol. 10 No. 198, 11 Jul. 1986 & JPA-61 40 568, (Kyowa Hakko Kogyo Co. Ltd.) 26-0-2-1986.
Michel Revel, et al., "Autocrine Interferons and Interferon-$\beta_2$", Jour. of Interferon Research, 7:529–536 (1987).
S. Marinkovic et al., "IL-6 Modulates the Synthesis of a Specific Set of Acute Phase . . . ", J. Immunol. Vol. 142, No. 3, 1989: 808–812.
Zilberstein, A. et al., "Structure & Expression of cDNA and Genes for Human Interferon . . . ", The EMBO Journal vol. 5, No. 10, pp. 2529–2537, 1986.

Primary Examiner—Richard A. Schwartz
Assistant Examiner—Joan Ellis
Attorney, Agent, or Firm—Nixon & Vanderhye

[57] ABSTRACT

Interferon $\beta_2$ has been identified as the major factor responsible for stimulating hepatocytes to produce antiinflammatory agents. A method for its use in so stimulating hepatocytes is described herein.

5 Claims, No Drawings

TREATING INFLAMMATION WITH HEPATOCYTE STIMULATING FACTOR INTERFERON $\beta_2$

FIELD OF THE INVENTION

This invention relates to factors which modulate inflammation.

BACKGROUND OF THE INVENTION

Inflammation occurs in response to tissue injury or infection. The acute inflammatory response is marked by fever, increased vascular permeability, alterations in plasma metal and steroid concentrations and leukocytosis. Associated with the leukocytosis and localization of the leukocytes to the injured or affected tissue is the release of a barrage of proteolytic enzymes of various specificities which degrade affected tissue and/or invading organisms. Control of acute inflammation must be regulated by the body to prevent hyperaccumulation of inflammation-causing agents and thereby avoid degradation of healthy tissue. One pathway of control is the stimulation of liver cells, i.e. hepatocytes, to produce a series of plasma proteins known collectively as acute phase proteins. The acute phase proteins include antiproteases which inactivate proteolytic enzymes released at the site of injury, clotting and complement components, opsonins and carrier proteins along with others of unknown function. The acute phase proteins include $\alpha 1$ acid glycoprotein, $\alpha 1$ proteinase inhibitor ($\alpha 1$ antitrypsin), $\alpha 1$ antichymotrypsin, haptoglobin, hemopexin and fibrinogen in most species along with C-reactive protein, C3 and Factor B complement components and serum amyloid A protein in man and in addition $\alpha 2$ macroglobulin and $\alpha 1$ cysteine proteinase inhibitor (major acute phase protein) in the rat.

Some medical conditions are due to an abundance of inflammatory mediators and proteins. Septacemia, or acute pancreatitis, for example, may result in an excess of proteolytic enzymes being released and marked tissue destruction. Conditions such as this may be due to an inadequate release of acute phase proteins to limit inflammation. On the other hand, post-surgery recovery in some patients is associated with infection and poor wound healing which may be due to an inadequate inflammatory response or an excessive anti-inflammatory response. Accordingly, it is possible that once the identity of the liver stimulant is known therapies designed to compensate for its absence or malfunction can remedy such conditions as septacemia and related conditions.

REFERENCE TO THE PRIOR ART

It has been shown recently that while the soluble factors interleukin-1 (IL-1) and tumor necrosis factor (TNF) are able to induce a restricted acute phase response in vitro (see Gauldie et al (1987) Immunology 60, 203-207) the major hepatic acute phase protein response is controlled by a separate factor, originally described as fibrinogen stimulating factor and more recently known as hepatocyte stimulating factor (HSF) (see Ritchie and Fuller (1983) N.Y. Acad. Sci, 408, 4990-5,000; Koj et al (1984) Biochem J. 224, 505-514 and Baumann et al (1983) J. Biol. Chem. 258, 563-570). The soluble factors IL-1 and TNF control only a subset of genes encoding the many acute phase proteins in man and rodents, while HSF, of either keratinocyte or peripheral blood monocyte origin, controls the remaining and to some extent all the gene expression of the acute phase proteins.

Characterization and identification of the hepatocyte stimulating factor have yet to be completed. Much more investigation is needed to elucidate the biochemical nature of this factor in order to take advantage of its properties in a therapeutic sense.

SUMMARY OF THE INVENTION

In their efforts to identify the factor which stimulates hepatocytes to produce acute phase proteins, the present inventors have made a surprising discovery. The hepatocyte stimulating factor is biochemically, immunologically and functionally identical to the known factor inteferon $\beta_2$. The common identity of these two factors is particularly surprising in that interferon $\beta_2$ has not heretofore been considered to be involved in modulation of the liver and the inflammatory response. Its primary function is thought to be as an anti-viral agent although it is generally recognized that of the known interferons, interferon $\beta_2$ elicits a weak anti-viral effect. Moreover, whereas the hepatocyte stimulating factor described in the literature was thought to arise solely from activated macrophages and monocytes, interferon $\beta_2$ is known to be produced by virus stimulated (poly I:C) fibroblasts. The functions and target cells or tissues for interferon $\beta_2$ are described only as either anti-viral or more recently as targeted to the B-lymphocyte cell. None of the activities of interferon $\beta_2$ described in the available literature is related to the liver or to acute phase protein gene regulation.

Accordingly, the present invention is based on applications of the knowledge herein provided that the hepatocyte stimulating factor is characteristically and biochemically the same substance as interferon $\beta_2$.

In one aspect, the present invention comprises, as a new use for interferon $\beta_2$, the method of stimulating hepatocytes to produce acute phase proteins which comprises treating hepatocytes in vivo with a hepatocyte stimulating amount of interferon $\beta_2$. Treatment may be conducted using, for example, injectable dosage forms for administration either intraparenterally or intravenously.

A further aspect of the invention comprises a composition of matter comprising interferon $\beta_2$ and a physiologically tolerable carrier. According to embodiments of the invention, such compositions comprise interferon $\beta_2$ in aqueous dosage form, such as buffered saline solutions of interferon $\beta_2$. Ampoules containing powdered interferon $\beta_2$ suitable for aqueous reconstitution as an injectable are also within the scope of the invention.

In addition to providing methods and compositions useful in stimulating hepatocyte production of acute phase proteins, the present invention comprises, in other aspects, immunoassays designed to determine the presence or concentration of the hepatocyte stimulating factor, interferon $\beta_2$, in a fluid sample, such as serum, obtained from the individual that has been injured or infected or whose tissue is suspected of being so affected.

The substance interferon $\beta_2$ is reported to be encoded by the cDNA sequence as reported by Weissenbach et al (1980) PNAS 77, 7152-7156. Substantially the same DNA sequence has been reported to code for a soluble factor known as B-cell stimulating factor (BSF-2) as reported by Hirano et al (1986) Nature 324, 73-76, to code for a 26kD protein and to code for hybridoma plasmacytoma growth factor (HGF). These relationships are summarized for example in Science 325, p. 582-583; and Science Vol. 235, p. 731-732. Accordingly, as the term is used herein, "interferon $\beta_2$" includes by definition those substances known presently in the literature as BSF-2, HGF and 26kD protein.

It will be appreciated by those skilled in the art that polymorphic forms of interferon $\beta_2$ and glycosylated forms thereof are likely to be produced naturally, being expressed by allelic variations of the DNA sequences reported to date as being interferon $\beta_2$ coding sequences (or BSF-2 or 26kD protein coding sequences). Provided, however, that these polymorphic forms of interferon $\beta_2$ have a polypeptide component which shares the biological function known presently for interferon $\beta_2$ and, importantly, shares the herein described function of stimulating hepatocytes to produce acute phase proteins, such polymorphic forms of interferon $\beta_2$ are useful in the present invention and are encompassed herein by the term "compounds having substantially the same biological function and biochemical identity as interferon $\beta_2$".

DESCRIPTION OF THE PREFERRED EMBODIMENTS

Processes for preparing the hepatocyte-stimulating interferon $\beta_2$ useful herein are described in the literature and are not repeated here in any great detail. Interferon $\beta_2$ may be prepared, for example, by extracting the compound from lipopolysaccharide-induced monocytes or from poly I:C-induced fibroblasts, but the processes for producing recombinant interferon $\beta_2$ are able to produce greater quantities more conveniently and are therefore preferred. One method for producing recombinant interferon $\beta_2$ is described by Hirano et al in Nature, Volume 324, Nov. 6, 1986, incorporated herein by reference. The recombinant interferon $\beta_2$ produced by this method will have an apparent molecular weight between 23 and 30 kD, an isoelectric point around 5.0 and will have the partial amino acid sequence described by Hirano et al, supra.

The method of the present invention, in which hepatocytes are stimulated to produce acute phase proteins, can be conducted by treating the hepatocytes with interferon $\beta_2$ admixed with any suitable carrier. Parenteral or intravenous administration is preferred in order to introduce the interferon $\beta_2$ to the hepatocytes. Accordingly, injectable solutions of interferon $\beta_2$ are preferred herein and may be formulated using protocols well established by the pharmaceutical industry. For example, compositions comprising interferon $\beta_2$ and a physiologically tolerable vehicle, such as saline or phosphate buffered saline, optionally in combination with a solubilizing agent for the active ingredient, such as mannitol, are suitable for administration.

Hepatocyte stimulating amounts of interferon $\beta_2$ will be in the range from about 1 to about 500 $\mu$g/kg body weight of the individual to be treated. Accordingly, compositions suitable for use in the method of the present invention will comprise interferon $\beta_2$ in an amount which reflects this range. Unit doses may be formulated for single injection of required interferon $\beta_2$, perhaps more appropriately, for repeated injection or by intravenous 'drip' to attain desired in vivo levels of interferon $\beta_2$ and thereby reduce the risk of toxic side effects. It should be noted that physiologically tolerable carriers should be selected to exclude those carriers which are apt to cause inflammation even to a minor extent.

Administration of interferon $\beta_2$ to stimulate hepatocyte production of acute phase proteins could either compensate for the body's inability to produce interferon $\beta_2$ in response to tissue injury or invasion or could augment the acute phase protein response in cases where sufficient functional interferon $\beta_2$ is not naturally produced.

In order for these conditions to be diagnosed, there is provided, in accordance with the present invention, a diagnostic assay designed to detect the presence or concentration of an anti-interferon $\beta_2$-binding substance in a fluid sample extracted from a patient. In principle, such an assay does not differ significantly from standard immunoassays described in the art for assaying other biological substances representative of other conditions or diseases e.g. assaying for HCG to diagnose pregnancy, etc. Antibody against interferon $\beta_2$ may be raised in rabbits, goats, sheep etc., recovered and then used to detect the presence of or to determine the concentration of its binding partner, interferon $\beta_2$. Preferably, antibody to interferon $\beta_2$ is immobilized e.g. covalently by cross-linking, on a solid support, such as latex beads, polystyrene wells or beads, polymeric membranes or filters, and then incubated with serum to permit binding. Bound interferon $\beta_2$ may be detected using any one of several techniques available in the art but preferably using a labelled sandwiching antibody for the captured interferon $\beta_2$ and then detecting the label bound in the assay. It is likely that background levels of interferon $\beta_2$ will persist in healthy individuals. Accordingly, diagnosis of conditions caused by inadequate serum levels of functional interferon $\beta_2$ will require an appraisal of the relative availability of interferon $\beta_2$ in a patient's serum with the interferon $\beta_2$ serum level found in healthy individuals. The reference serum level of interferon $\beta_2$ can easily be determined by assaying a representative number of serum samples from a control population. Clearly, those individuals with visible tissue injury/inflammation testing negative for interferon $\beta_2$ levels in the serum assay are candidates for interferon $\beta_2$ administration.

The assay described herein may also be used to detect tissue injury. Acute phase proteins will normally appear in serum about 24 hours after injury. Accordingly, the presence of interferon $\beta_2$ in serum, which stimulates liver to produce the acute phase proteins, should be present in the serum, and may therefore be assayed, within 24 hours from injury. Such an assay is similar in purpose to known assays which determine the presence or concentration of acute phase proteins in the serum. However, because the assay for IFNB$_2$ is designed to detect the agent responsible for liver stimulation rather than the result of that stimulation, the IFNB$_2$ assay can be used to detect tissue injury much earlier than is possible with known methods. This is especially important in situations where tissue injury is internal, i.e. cannot be diagnosed by observation. By providing a rapid assay for IFNB$_2$, physicians are provided with a means for assessing internal injury prior to acute phase protein production and without surgical exploration.

IDENTIFICATION OF HEPATOCYTE STIMULATING FACTOR

The experimental protocol used to produce, identify and assess the function of hepatocyte stimulating factor is described hereinbelow and is followed by data generated in the experiments.

To prepare hepatocyte stimulating factor as defined by established criteria, human peripheral blood monocyte conditioned medium was prepared as previously described by Koj et al in Immunology (1987) 60, 203-207. In brief, monocytes, separated by buoyant density centrifugation and further purified by adherence, were stimulated with 10 µg/ml lipopolysaccharide (*E. coli* 055:85, TCA extracted, Sigma, St. Louis) for 24 h at 37° C. The supernatant was dialysed (Spectropore 6-8000) against phosphate buffered saline and filter-sterilized.

To obtain interferon $\beta_2$ as defined by established criteria, human fibroblast conditioned medium (Fib-CM) was obtained from primary human lung fibroblast lines which have been established from normal lung explants (see Jordana et al, J. Leukocyte Biol., in press). Supernatants from fibroblasts cultured in DMEM medium with 10% fetal calf serum or from cells cultured in serum free medium containing various concentrations (5-20 IU/ml) of platelet-derived growth factor (PDGF) (Collaborative Research) and cultured for 24 h, were dialysed and filter sterilized.

Regulation of plasma protein production by the selected soluble factor was analyzed using human hepatoma cells (HepG2) and primary cultures of rat hepatocytes as previously described by Baumann (1987) J. Biol. Chem. and by Koj et. al. (1985) J. Immunol. Methods, 76, 317-327. HepG2 cells were maintained in Dulbecco's Modified Eagle Medium (DMEM) containing 10% heat-inactivated FCS and passaged every 10 to 14 days prior to being treated in the experimental assay. Primary cultures of rat hepatocytes were prepared from adult Sprague-Dawley rats by collagenase perfusion and adherence isolation as described by Koj et. al. (1985) supra.

Hepatocyte stimulation activity and induction of acute phase protein synthesis was carried out as described by Baumann (1987) supra for HepG2 cells and as described by Koj et. al. (1985) supra for rat hepatocytes. A unit of HSF activity is that concentration required to induce one-third of the maximal stimulation of $\alpha 1$ antichymotrypsin, serving as a representative acute phase protein, in HepG2 cells and one half of the maximal stimulation of $\alpha$-2 macroglobulin in rat hepatocytes. The assays have previously been shown to be reproducible having an assay coefficient of variation, CV, of 4% and between assay CV of 10%. In each case, the cells were exposed to soluble factor-containing medium for various times by repeated addition in fresh media. The amounts of acute phase proteins secreted into the medium during a set period of time during the final period of exposure in culture was determined by rocket immunoelectrophoresis using monospecific antisera for the various proteins, as described by Koj et. al. (1984) Biochem J. 224, 505-514 and by Baumann et. al. J. Biol. Chem. 258, 563-570.

The assay for lymphocyte activating factor activity of interleukin-1 (IL-1) preparations was carried out using the PHA co-stimulator assay and C3H/HaJ thymocytes as described by Koj et. al. 1984, supra.

Antibody preparations and neutralizations used herein include: rabbit anti-human recombinant tumor necrosis factor; rabbit anti-human recombinant interleukin-1$\beta$; rabbit anti-human recombinant 1$\alpha$; rabbit anti-interferon $\beta$, (one ml neutralizes 1,000 units of 1FN$\beta_2$ activity); sheep anti-IFN$\beta$ (N.I.H. research reference reagent, cat. no. G-028-501-568) and control sheep antiserum; calf anti-IFN$\beta_1$ and $\beta_2$ and monoclonal anti-human IFN$\beta$ (Boehringer Mannheim, cat. no. 853577). Absorptions with the various antisera were carried out by incubating a standard pool sample of PBM-CM with increasing amounts of each antibody and control serum. The supernatant was incubated 1 h, 37° C., filter sterilized and tested in the hepatocyte assay and LAF assay for residual activity. Recombinant cytokines were also used, including recombinant purified human TNF ($5 \times 10^7$ U/mg); recombinant purified human IL-1$\alpha$ ($6 \times 10^8$ units/mg) and IL-1$\beta$ ($2 \times 10^8$ U/mg) and recombinant purified human BSF-2 (IFN$\beta_2$) ($2 \times 10^5$ U/ml).

To examine the identity of the hepatocyte stimulating factor, the effect of preincubation with various antibody preparations on the HSF activity of perepheral blood monocyte cultured medium, which contains a complex mixture of these various activities. Using a standard stimulus of PBM-CM, preabsorption with anti-IL-1$\alpha$ and anti-IL-1$\beta$ removed all of the lymphocyte activating factor (LAF) activity, 80% of the $\alpha 1$ acid glycoprotein induction and 20-25% of the albumin reduction. Similar trends are observed following absorption of PBM-CM with anti-TNF. Since these antibodies are polyclonal and raised against recombinant material, lack of reactivity with HSF would rule out a serologic relationship between these cytokines. There was no change in $\alpha 2$ macroglobulin induction, while there was an apparent increase in the induction of fibrinogen and cysteine proteinase inhibitor, indicating that removal of IL-1 does not remove HSF and that IL-1 may actually inhibit the production of these two molecules. Absorption with either sheep or calf anti-interferon $\beta$ (active against IFN$\beta_1$ and IFN$\beta_2$) totally removed the HSF activity ($\alpha 2$ macroglobulin, fibrinogen, etc.) but did not alter the LAF content of the supernatant. Absorption with a combination of anti-IFN$\beta_2$ and anti-IL1$\alpha$, $\beta$ removed all activities causing acute phase protein induction from PBM-CM. Absorption with specific anti-IFN$\beta_1$, either polyclonal or monoclonal, did not alter any of the responses. All control absorption (normal rabbit, sheep, calf sera) had no significant effect on any of the activities.

Having shown immunologic identity between monocyte HSF and an activity recognized by anti-fibroblast derived IFN$\beta$, as described above, it was then determined whether primary human lung fibroblast lines exhibited an HSF activity. Table 1 shows that supernatants from human lung fibroblasts, either constitutively or under conditions of stimulation with PDGF, caused significant stimulation of the same spectrum of acute phase proteins by human (Table 1A) and rat (Table 1B) hepatocytes.

TABLE 1A

| Treatment | KepG2 Cells Secretion (µg/24 hrs/$10^6$ cells) | | | |
|---|---|---|---|---|
| | Fibrinogen | ACH | AGP | HP |
| control | 0.1 | 1.3 | 0.3 | .4 |
| rIl-1$\beta$ (250 units/ml) | <.01 | 3.1 | 1.8 | 1.2 |
| PBM-CM (1:20) | 0.4 | 11.6 | 5.8 | 2.2 |
| HSF (20 units/ml) | 1.0 | 8.0 | 1.1 | 1.2 |
| Fibroblast-CM (1:10) | 1.4 | 8.1 | 0.9 | 1.5 |
| rIFN$\beta$2/BSF-2 (60 units/ml) | 1.7 | 9.9 | 1.4 | 1.7 |

TABLE 1B

| | Rat Hepatocytes | | |
|---|---|---|---|
| | Secretion ($\mu$g/24 hrs/$10^6$ cells) | | |
| Treatment | α2-macro | CPI | albumin |
| control | 7 | 26 | 40 |
| rIL-1β (250 units/ml) | 8 | 23 | 33 |
| PBM-CM (1:20) | 50 | 30 | 13 |
| HSF (20 units/ml) | 45 | 35 | 14 |
| Fibroblast-CM (1:10) | 42 | 33 | 29 |
| rIFNβ2/BSF-2 (60 units/ml) | 46 | 38 | 14 |

The same supernatant did not exhibit any IL-1 activity in an LAF assay. The amount of HSF activity in fibroblast CM was approximately equal, on a per cell basis, to that found in PBM-CM.

With the antibody and fibroblast-CM studies suggesting identity, it was next determined whether purified *E. coli*-derived human recombinant BSF-2 could duplicate the effects of PBM-derived HSF. Purified human rBSF-2(IFNβ2), showed a dose-dependent stimulation of human HepG2 cells and primary rat hepatocytes with the identical spectrum of acute phase protein gene expression as can be seen with PBM derived HSF and fibroblast HSF. Not only were the various proteins induced, but albumin was coincidentally decreased in synthesis by IFNβ2/BSF-2. Maximum stimulation of α2 macroglobulin synthesis by rat hepatocytes or fibrinogen synthesis by HepG$_2$ cells was achieved with 60 units of BSF-2 and with 40 units of PBM derived HSF. Absorption of the purified rBSF-2 with either sheep or calf anti-IFN-β totally inhibited the HSF activity caused by the recombinant molecule.

Thus, attempts to purify the molecular activity responsible for the major acute phase protein induction showed that LPS-activated monocytes released a hepatocyte stimulating factor which stimulates the production of all of the antiproteinases (cysteine proteinase inhibitor, α2 macroglobulin, contrapsin, α1 antitrypsin), hemopexin and fibrinogen in a major way, while having a lesser but significant stimulating effect on the synthesis of α1 acid glycoprotein, haptoglobin and C3. Thus this activity represents a full spectrum HSF. HSF and IL-1β along with permissive levels of glucocorticoid are likely to represent the full content of hepatocyte specific activities in PBM conditioned medium.

The similar molecular characteristics that were initially noted between monocyte-derived HSF and hybridoma growth factor (recently shown to be identical to interferon β2) was confirmed by the antibody absorptions of PBM conditioned media as described above. Antibodies raised against human fibroblast derived interferon β, having activity against interferon β$_1$ and β$_2$ were able to neutralize the HSF activity leaving only the IL-1 mediated hepatocyte activity and LAF activity. Further absorption with anti-IL-1, which could not neutralize the HSF activity, indicating the lack of serologic identity between HSF and IL-1, effectively removed the remaining hepatocyte specific activity. Antibodies specific for interferon β$_1$ had no effect on HSF or LAF activity. Thus, most if not all of the hepatocyte stimulating activity in human monocytes is due to the presence of a molecule recognized by anti-interferon β$_2$ and to the presence of IL-1β. In addition, it has been found that both sources of anti-interferon β$_2$ antisera could immunoprecipitate a 23-26 kD protein from 35S-methionine labelled monocyte supernatants confirming reports that the 1.3 kd IFNβ$_2$ mRNA is expressed in human monocytes (see Vaquero(1986) J. Interferon Res. 6, 161-167).

It has also herein been shown that fibroblasts release a molecule causing identical stimulation of hepatocytes as does monocyte HSF (Table 1) and were able to totally absorb out this activity with the same anti-IFNβ$_2$ that neutralized HSF. This neutralization could remove all hepatocyte stimulating activity when the fibroblast conditioned media contained no IL-1 or TNF. Thus the monocyte HSF is serologically related to fibroblast HSF and in turn to fibroblast IFNβ$_2$.

We claim:

1. A method for treating inflammation in a mammal by stimulating acute phase protein production in said mammal, said method comprising the step of administering thereto a hepatocyte stimulating amount of interferon B-2.

2. The method according to claim 1 wherein said hepatocyte stimulating amount is in the range of from 1 to 500 $\mu$g per kg body weight of said mammal.

3. The method according to claim 1, wherein said heptocyte stimulating amount of interferon B-2 is administered by injection.

4. The method according to claim 3, wherein said heptocyte stimulating amount is administered intravenously.

5. The method according to claim 1, wherein said interferon B-2 is recombinant interferon B-2.

* * * * *